United States Patent
Whitehurst et al.

(10) Patent No.: US 8,676,322 B2
(45) Date of Patent: Mar. 18, 2014

(54) METHODS AND SYSTEMS OF TREATING PANCREATITIS PAIN

(75) Inventors: Todd K. Whitehurst, Valencia, CA (US); Kristen N. Jaax, Santa Clarita, CA (US); Rafael Carbunaru, Valley Village, CA (US); Greg Baldwin, Valencia, CA (US); Brett Schleicher, Valencia, CA (US); Andrew DiGiore, Santa Monica, CA (US); Roger Hastings, Maple Grove, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 746 days.

(21) Appl. No.: 12/358,073

(22) Filed: Jan. 22, 2009

(65) Prior Publication Data

US 2009/0192558 A1  Jul. 30, 2009

Related U.S. Application Data

(60) Provisional application No. 61/024,881, filed on Jan. 30, 2008.

(51) Int. Cl.
*A61N 1/05* (2006.01)

(52) U.S. Cl.
USPC .......................................................... 607/40

(58) Field of Classification Search
USPC ........................................ 607/9, 40; 600/439
See application file for complete search history.

(56) References Cited

U.S. PATENT DOCUMENTS

| | | | |
|---|---|---|---|
| 5,147,294 A | 9/1992 | Smith et al. | |
| 5,193,539 A | 3/1993 | Schulman et al. | |
| 5,193,540 A | 3/1993 | Schulman et al. | |
| 5,312,439 A | 5/1994 | Loeb | |
| 5,501,703 A | 3/1996 | Holsheimer et al. | |
| 5,727,556 A * | 3/1998 | Weth et al. | 600/439 |
| 5,938,688 A | 8/1999 | Schiff | |
| 6,016,449 A | 1/2000 | Fischell et al. | |
| 6,051,017 A | 4/2000 | Loeb et al. | |
| 6,164,284 A | 12/2000 | Schulman et al. | |
| 6,185,452 B1 | 2/2001 | Schulman et al. | |
| 6,208,094 B1 | 3/2001 | Morrish | |
| 6,208,894 B1 | 3/2001 | Schulman et al. | |
| 6,280,873 B1 | 8/2001 | Tsukamoto | |
| 6,381,496 B1 | 4/2002 | Meadows et al. | |
| 6,458,171 B1 | 10/2002 | Tsukamoto | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |

(Continued)

FOREIGN PATENT DOCUMENTS

| | | | |
|---|---|---|---|
| WO | WO 02/087653 A2 | 11/2002 | |
| WO | WO 2006/116165 A1 | 11/2006 | |
| WO | WO 2007/038200 A1 | 4/2007 | |
| WO | WO 2007/109656 A2 | 9/2007 | |

*Primary Examiner* — George Manuel
(74) *Attorney, Agent, or Firm* — Vista IP Law Group LLP

(57) ABSTRACT

Methods and systems of treating a patient with pancreatitis pain include providing a stimulator, configuring one or more stimulation parameters to treat pancreatitis pain, programming the stimulator with the one or more stimulation parameters, generating a stimulus configured to treat pancreatitis pain with the stimulator in accordance with the one or more stimulation parameters, and applying the stimulus with the stimulator to one or more stimulation sites in accordance with the one or more stimulation parameters.

26 Claims, 14 Drawing Sheets

(56) References Cited

U.S. PATENT DOCUMENTS

| | | |
|---|---|---|
| 6,596,439 B1 | 7/2003 | Tsukamoto et al. |
| 6,605,383 B1 | 8/2003 | Wu |
| 6,607,843 B2 | 8/2003 | Ruth, II et al. |
| 6,760,626 B1 | 7/2004 | Boveja |
| 6,761,715 B2 | 7/2004 | Carroll |
| 6,780,626 B2 | 8/2004 | Li et al. |
| 6,885,888 B2 * | 4/2005 | Rezai ................ 607/9 |
| 7,193,539 B2 | 3/2007 | Kim et al. |
| 7,501,703 B2 | 3/2009 | Minervini |
| 7,938,688 B2 | 5/2011 | Teramoto |
| 2002/0161360 A1 | 10/2002 | Carroll |
| 2004/0220648 A1 | 11/2004 | Carroll |
| 2007/0049793 A1 | 3/2007 | Ignagni et al. |
| 2007/0073354 A1 | 3/2007 | Knudson et al. |
| 2007/0106338 A1 | 5/2007 | Errico |
| 2007/0150009 A1 | 6/2007 | Kveen et al. |
| 2007/0225781 A1 | 9/2007 | Saadat et al. |
| 2008/0154333 A1 | 6/2008 | Knudson et al. |
| 2009/0192570 A1 * | 7/2009 | Jaax et al. ............. 607/46 |
| 2010/0174339 A1 * | 7/2010 | Pyles ................. 607/40 |

* cited by examiner

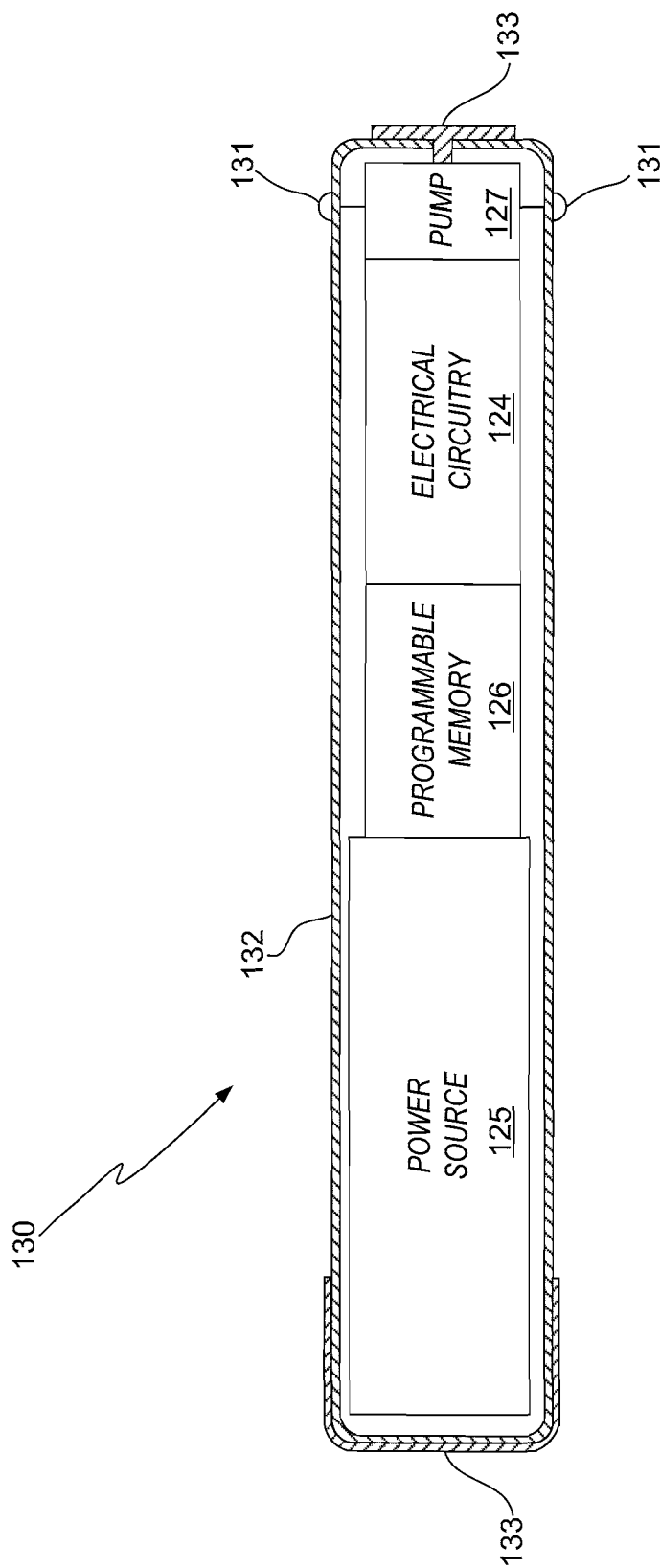

METHODS AND SYSTEMS OF TREATING PANCREATITIS PAIN

RELATED APPLICATIONS

The present application claims priority under 35 U.S.C. §119(e) to U.S. Provisional Patent Application No. 61/024,881 by Todd K. Whitehurst et al., filed on Jan. 30, 2008, and entitled "METHODS AND SYSTEMS OF TREATING PANCREATITIS PAIN," the contents of which are hereby incorporated by reference in their entirety.

BACKGROUND

The pancreas is a gland located deep in the abdomen between the stomach and the spine. The pancreas performs exocrine and endocrine functions. Its exocrine functions include secreting pancreatic juice containing digestive enzymes into the digestive tract. Its endocrine functions include producing hormones such as insulin, glucagon, and somatostatin, for controlled release into the bloodstream.

Chronic pancreatitis is an inflammatory condition that results in permanent structural changes in the pancreas. Clinical manifestations of this disorder include chronic abdominal pain and pancreatic exocrine and endocrine dysfunction.

One theory regarding the pathogenesis of chronic pancreatitis suggests that increased secretion of pancreatic proteins causes proteinaceous plugs to form within the interlobular and intralobular ducts of the pancreas. These plugs may acts as a nidus for calcification, leading to stone formation within the duct system. The net result is the formation of ductal epithelial lesions which scar and obstruct the pancreatic ducts, thereby causing inflammatory changes and cell loss.

When a patient suffers from a pancreatic or biliary duct obstruction, such as those encountered with pancreatitis, the production of pancreatic enzymes may be a damaging and painful process. Since there is a hindrance of the natural passage of these enzymes into the GI tract, digestive juices may build up within the pancreas, causing ductal distension, tissue damage, and pain. Due to the increased pressure in the duct, the fluid may seek alternate, unnatural routes for release, which may lead to the development of fissures in the pancreas. These fissures may leak pancreatic enzymes that digest surrounding tissues and organs and thereby cause severe abdominal pain and organ damage.

SUMMARY

Methods of treating a patient with pancreatitis pain include providing a stimulator, configuring one or more stimulation parameters to treat pancreatitis pain, programming the stimulator with the one or more stimulation parameters, generating a stimulus configured to treat pancreatitis pain with the stimulator in accordance with the one or more stimulation parameters, and applying the stimulus with the stimulator to one or more stimulation sites in accordance with the one or more stimulation parameters.

Systems for treating a patient with pancreatitis pain include a stimulator configured to generate at least one stimulus in accordance with one or more stimulation parameters adjusted to treat pancreatitis pain, a programmable memory unit in communication with the stimulator and programmed to store the one or more stimulation parameters to at least partially define the stimulus such that the stimulus is configured to treat the pancreatitis pain, and means, operably connected to the stimulator, for applying the stimulus to one or more stimulation sites.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 3 illustrates an exemplary microstimulator according to principles described herein.

Throughout the drawings, identical reference numbers designate similar, but not necessarily identical, elements.

DETAILED DESCRIPTION

Methods and systems for treating a patient with pancreatitis pain are described herein. As used herein, "pancreatitis pain" refers to any type of pain caused by other otherwise associated with pancreatitis and/or other pancreatic dysfunction. For example, pancreatitis pain may be caused by ductal hypertension, pancreatic enzyme buildup, pancreatic leakage, ductal occlusions or obstructions, pancreatic ischemia, inflammation, improper pancreatic enzyme secretion, and/or any other pancreatic dysfunction.

In some examples, a stimulator may be configured to apply at least one stimulus to one or more stimulation sites in accordance with one or more stimulation parameters. The stimulus is configured to treat pancreatitis pain and may include electrical stimulation and/or drug stimulation. The stimulus may be used to decrease chronic pancreatitis pain due to ductal hypertension, pancreatic enzyme buildup, pancreatic leakage, and ductal obstructions. As used herein, "treating" pancreatitis pain refers to any amelioration or prevention of one or more causes, symptoms, and/or sequelae of pain resulting from pancreatitis and/or other pancreatic dysfunction.

A number of advantages are associated with the systems and methods described herein. For example, the techniques used to implant the stimulator may be minimally invasive and carry a low risk of external scarring. The procedures described herein for treating pancreatitis pain may be reversible in that implanted devices may be turned off and/or removed at any time. Moreover, adjustments to the stimulation parameters may be made throughout the treatment period by reprogramming the implanted stimulator via, for example, a transcutaneous communication link.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

To facilitate an understanding of the systems and methods described herein, a brief overview of the etiology of pancreatitis and pancreatitis pain will be given in connection with FIGS. 1A and 1B.

Figure 1A:
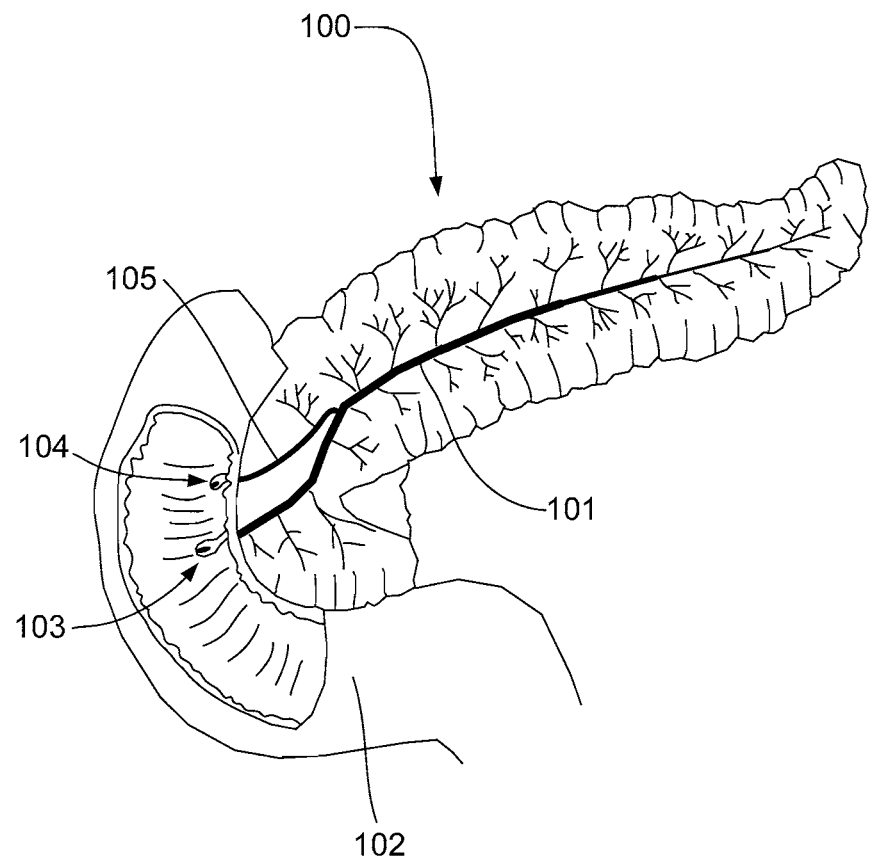
FIG. 1A is a front view of an exemplary human pancreas and a portion of the duodenum.

FIG. 1A is a front view of a human pancreas 100. As shown in FIG. 1A, the pancreas 100 is in direct contact with the duodenum 102, which is the first part of the small intestine and responsible for the breakdown of food within the small intestine. The pancreas 100 includes both endocrine and exocrine tissue. Endocrine tissue produces and secretes hormones such as insulin, glucagon, somatostatin, and others into the bloodstream level. Exocrine tissue produces and secretes into the duodenum 102 pancreatic juice containing enzymes (e.g., trypsin, chymotrypsin, and bicarbonate ions) that break down digestible foods within the digestive tract. As will be described in more detail below, pancreatitis and associated pancreatitis pain are often caused by pancreatic exocrine and endocrine dysfunction.

The exocrine tissue of the pancreas 100 includes a large number of ducts arranged in clusters referred to as acini. Pancreatic juices are first secreted into a lumen of each acinus. The juices accumulate within these ducts and eventually drain into a main duct known as the pancreatic duct 101. The pancreatic duct 101 empties directly into the duodenum 102 through a perforation known as the major duodenal papilla 103. Most people have only one main pancreatic duct 101, but in some cases a branch of the pancreatic duct 105 known as the accessory pancreatic duct 169 (alternatively referred to as the Duct of Santorini) also empties into the duodenum 102 at a perforation called the minor duodenal papilla 104.

Pancreatitis is a painful condition in which the pancreas 100 becomes inflamed. Pancreatitis may be chronic or acute. As mentioned, one theory regarding the pathogenesis of chronic pancreatitis suggests that ductal occlusions in the exocrine tissue of the pancreas 100 do not permit the proper flow of pancreatic juices through the pancreatic duct 101 and duodenal papilla 103, 104. This hindrance of the natural passage of pancreatic juices into the gastrointestinal tract may cause the pancreatic juices to build up within the pancreas 100, thus creating ductal distension, tissue damage, and pain. Due to the increased pressure in the pancreatic duct 101 and other ducts, pancreatic juices may seek alternate and unnatural routes for release which may consequentially lead to the development of fissures in the pancreas 100. These fissures may leak pancreatic enzymes that digest surrounding tissues and organs, leading to severe abdominal pain and organ damage.

Figure 1B:
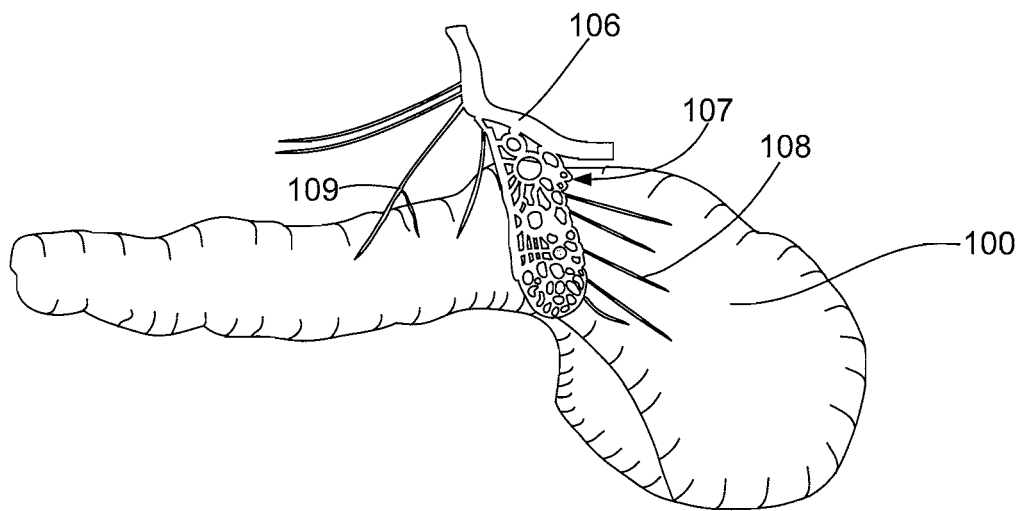
FIG. 1B is a dorsal view of an exemplary pancreas and a partial view of the innervation thereof.

FIG. 1B is a dorsal view of the pancreas 100 showing a partial innervation thereof. Many of the nerves that innervate the pancreas 100 extend from the distal end of the vagal trunk. The celiac trunk 106 is one such extension that innervates the pancreas. Neural tissue known as the celiac plexus 107 is located near where the celiac trunk 106, the superior mesenteric artery, and renal arteries branch from the abdominal aorta. Like other nerve plexuses, the celiac plexus 107 includes a network of interconnecting nerve fibers. The celiac trunk 106, the celiac plexus 107, nerve branches thereof (e.g., 108 and 109), and other neural tissue serve to innervate the pancreas 100. In particular, these nerves may innervate the exocrine tissue of the pancreas 100 and help regulate the exocrine functions of the pancreas 100.

It is believed that applying a stimulus to one or more stimulation sites within a patient may be useful in treating pancreatitis pain. As used herein, the term "stimulation site" may refer to one or more regions of the pancreas and/or one or more nerves that innervate the pancreas. For example, the stimulation site may include, but is not limited to, one or more nerves that innervate exocrine and/or endocrine tissue of the pancreas, the celiac trunk or branches thereof, one or more of the sympathetic or parasympathetic nerves surrounding or near the celiac trunk, one or more nerves surrounding or near the superior mesenteric vein or artery, the dorsal root ganglion, one or more dorsal columns and/or roots, the sympathetic trunk, the sympathetic ganglia, one or more levels of the spinal cord (e.g., C1-C4 and/or T4-L2), one or more somatic nerves in or around the pancreas, exocrine tissue within the pancreas, endocrine tissue within the pancreas, and/or any other tissue of the pancreas.

In some examples, as will be described in more detail below, the stimulus may be configured to block neural signals relating to nociceptive or chronic pain in the pancreas and/or surrounding organs, thus providing relief to a patient from pancreatitis pain. Additionally or alternatively, the stimulus may be configured to suppress pancreatic digestive activity, suppress production of pancreatic enzymes, and/or eliminate or decrease pancreatic juice buildup to reduce the damaging effects of pancreatitis and the pain associated therewith.

For example, the stimulus may be configured to block the vagal efferents and/or pancreatic ganglia that innervate acinar cells (which produce digestive enzymes) within the pancreas, thereby suppressing the production of these enzymes. Similarly, by blocking the specific vagal afferents associated with the aforementioned efferents, the systems and methods described herein may be able to curb enzymatic production in the pancreas. Additionally or alternatively, the stimulus may be configured to prevent contraction in exocrine tissue around obstructions in the pancreatic duct or other exocrine ducts.

Consequently, a stimulator may be implanted within a patient to deliver a stimulus to one or more of the stimulation sites described herein to treat pancreatitis pain. The stimulus may include an electrical stimulation current and/or the infusion of one or more therapeutic drugs at the stimulation site.

As used herein, and in the appended claims, the term "stimulator" will be used broadly to refer to any device that delivers a stimulus to a stimulation site to treat pancreatitis pain. Thus, the term "stimulator" includes, but is not limited to, a microstimulator, implantable pulse generator (IPG), spinal cord stimulator (SCS), external trial stimulator, system control unit, deep brain stimulator, drug pump, or similar device.

Figure 2:
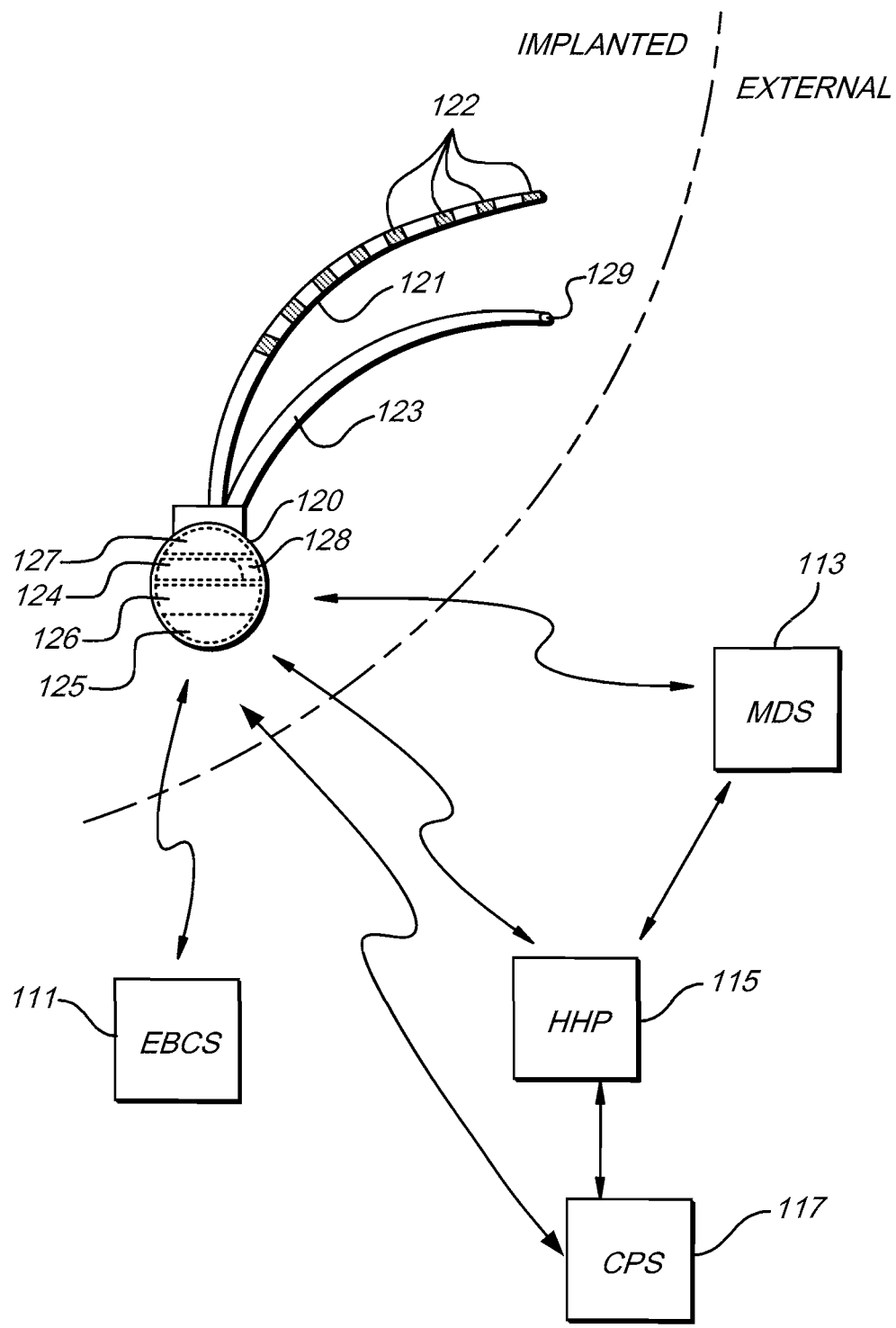
FIG. 2 illustrates an exemplary implantable stimulator according to principles described herein.

A more detailed description of an exemplary stimulator and its operation will now be given in connection with FIG. 2. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application. In some alternative examples, as will be described in more detail below, the stimulator 120 may be leadless.

As illustrated in FIG. 2, the stimulator 120 includes a number of components. It will be recognized that the stimulator 120 may include additional and/or alternative components as best serves a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607, 843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 111 may be provided to generate power that is used to recharge the power source 125 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120.

Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump 127 may also be included within the stimulator 120. The pump 127 may be configured to store and dispense one or more drugs, for example, through a catheter 123. The catheter 123 may be coupled at a proximal end to the stimulator 120 and may have an infusion outlet 129 for infusing dosages of the one or more drugs at the stimulation site. In some embodiments, the stimulator 120 may include multiple catheters 123 and/or pumps for storing and infusing dosages of the one or more drugs at the stimulation site.

The one or more drugs that may be applied to a stimulation site to treat pancreatitis pain may have an analgesic effect on the stimulation site. For example, an opiate or other narcotic may be administered at the stimulation site coupled with a low dose of amitriptyline and a nonsteroidal anti-inflammatory drug. In additional or alternative embodiments, the one or more drugs may include a hormonal enzyme suppressant or a digestive enzyme configured to suppress hormonal feedback loops in the duodenum 102. By suppressing enzyme production in the exocrine regions of the pancreas, pancreatitis pain may be alleviated or reduced.

Additionally or alternatively, the one or more drugs may have an excitatory or inhibitory effect on the stimulation site (e.g., to suppress digestive activity of the pancreas, suppress production of pancreatic enzymes, and/or eliminate or decrease pancreatic juice buildup).

Exemplary drugs that may be applied to a stimulation site to treat pancreatitis pain include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat pancreatitis pain include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat pancreatitis pain include, but are not limited to, steroids, antibiotics, anticonvulsants, antidepressants, and gangliosides. These compounds have been shown to increase efficacy of drug infusion, reduce fibrosis, and/or prevent infection.

Any of the drugs listed above, alone or in combination, or other drugs or combinations of drugs developed or shown to treat pancreatitis pain may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus.

Specific stimulation parameters may have different effects on different types, causes, or symptoms of pancreatitis pain. Thus, in some examples, the stimulation parameters may be adjusted at any time throughout the treatment course as best serves the particular patient being treated. It will be recognized that any of the characteristics of the stimulation current, including, but not limited to, the pulse shape, amplitude, pulse width, frequency, burst pattern (e.g., continuous or intermittent), duty cycle or burst repeat interval, ramp on time, and ramp off time may be adjusted throughout the course of treatment as best serves a particular application.

To illustrate, a baseline set of stimulation parameters may initially be set to begin treatment of pancreatitis pain. These baseline values may be adjusted throughout the course of treatment in response to patient feedback or sensed indicators of pancreatitis pain. Additionally or alternatively, the patient and/or clinician may adjust the stimulation parameters at any time to prevent accommodation, collateral stimulation, and/or ineffectiveness.

In some embodiments, the stimulation parameters may be configured to provide monopolar electrical stimulation. For example, an external case of the stimulator 120 may be used as an indifferent electrode. In other embodiments, the stimulation parameters may be configured to provide bipolar electrical stimulation (e.g., one of the electrodes 122 may be used as an indifferent electrode). Different stimulation parameters may have different effects on neural or other tissue. Therefore, parameters may be chosen to target specific neural or other tissue populations and/or exclude others in order to achieve a desired therapeutic effect. Additionally, the stimulation parameters may provide for current steering between electrodes 122 such that specific stimulation sites may be targeted.

An exemplary baseline set of stimulation parameters that may be used to initially define stimulation current that is used to treat pancreatitis pain includes, but is not limited, to the stimulation parameters shown in Table 1. It will be recognized that the baseline set of stimulation parameters shown in Table 1 may vary depending on the particular patient being treated and that additional or alternative stimulation parameters may be defined.

TABLE 1

Exemplary Baseline Stimulation Parameters

| Stimulation Site Nerve Type | Activating Frequency | Inhibiting Frequency | Pulse Width |
|---|---|---|---|
| Parasympathetic | 1-50 Hz | >100 Hz | 10 μsec-5 msec |
| Sympathetic | 1-100 Hz | >100 Hz | 10 μsec-5 msec |

Hence, as shown in Table 1, a stimulation current having a pulse width of 10 μsec-5 msec and may be initially applied to one or more parasympathetic and/or sympathetic nerves that innervate the pancreas and/or surrounding organs in order to treat pancreatitis pain. The pulse width and amplitude may be configured so as to avoid muscle spasms, nerve damage, and/or discomfort.

As shown in Table 1, the frequency of the stimulation current may depend on the type of nerve tissue being targeted. For example, an activating frequency of 1-50 Hz may be applied to parasympathetic nerves and an activating frequency of 1-100 Hz may be applied to sympathetic nerves.

In some examples, these baseline parameters may be determined in the initial fitting session and may depend on the electrode placement (e.g., how proximal they are to the stimulation site), local impedance (which may be affected by scar tissue, etc.), and patient variability. The clinician or other programmer may make subtle, iterative adjustments to any of the stimulation parameters in response to real-time feedback from the patient.

After a predetermined length of time (e.g., a week, a month, or multiple months) of treatment or as the need may arise, the patient may be evaluated to determine whether the stimulation parameters need to be adjusted and/or whether the additional stimulation is needed in order to treat the pancreatitis pain. In some examples, if the patient no longer exhibits any symptoms of pancreatitis pain, the stimulation may be terminated. Alternatively, if it is determined that the patient needs further treatment, the stimulation may continue in accordance with the same set of stimulation parameters or in accordance with a newly defined set of stimulation parameters. For example, the stimulation parameters may be adjusted from the exemplary baseline stimulation parameters described previously in connection with Table 1 to have values that better suit the needs of the patient and more effectively treat pancreatitis pain.

Due to the fact that increased pancreatic enzyme production during heightened levels of gastrointestinal activity tend to exacerbate pancreatitis pain in some patients, the stimulation parameters of the stimulator 120 may be configured to provide lower levels of stimulation during periods where gastrointestinal activity is relatively low (e.g., between meals) and higher levels stimulation during periods of relatively higher gastrointestinal activity (e.g., during and after meals).

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, or any other type of implantable device configured to deliver a stimulus to a stimulation site within a patient.

Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501, 703; 6,487,446; and 6,516,227. Exemplary deep brain stimulators suitable for use as described herein include, but are not limited to, those disclosed in U.S. Pat. Nos. 5,938,688; 6,016, 449; and 6,539,263. All of these listed patents are incorporated herein by reference in their respective entireties.

The stimulator 120 of FIG. 2 may alternatively include a microstimulator. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, and the pump 127 described in connection with FIG. 2. These components are housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface thereof.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4A:
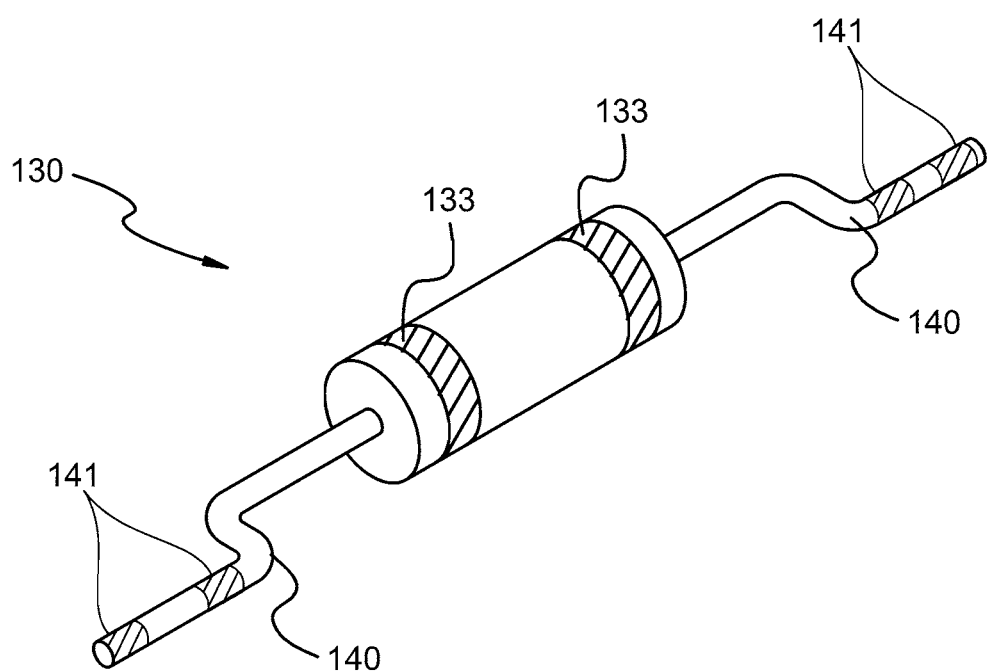
FIG. 4A shows an example of a microstimulator with one or more leads coupled thereto according to principles described herein.
Figure 4B:
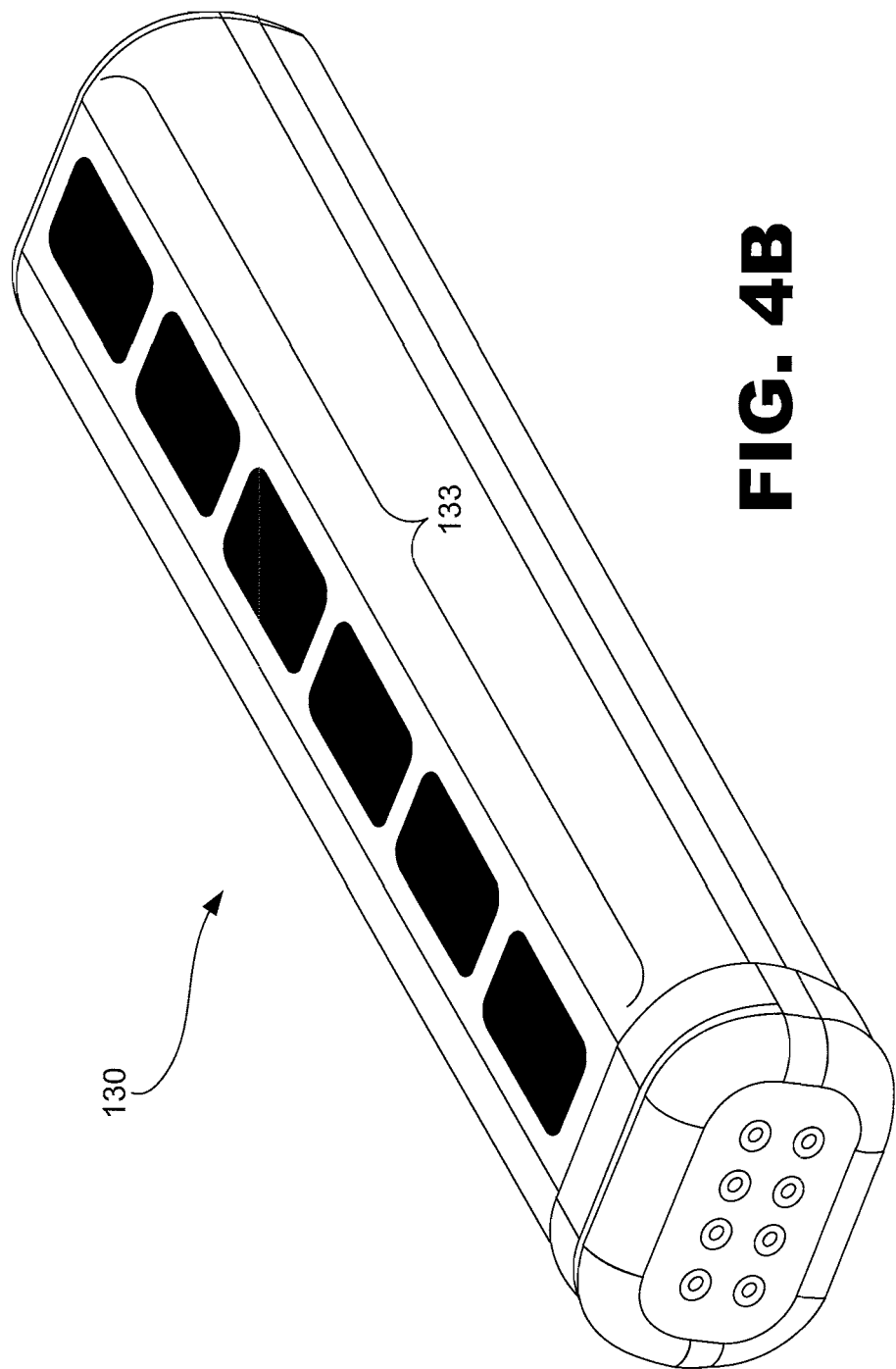
FIG. 4B shows an example of a microstimulator with a plurality of electrodes disposed on an outer surface thereof according to principles described herein.
Figure 4C:
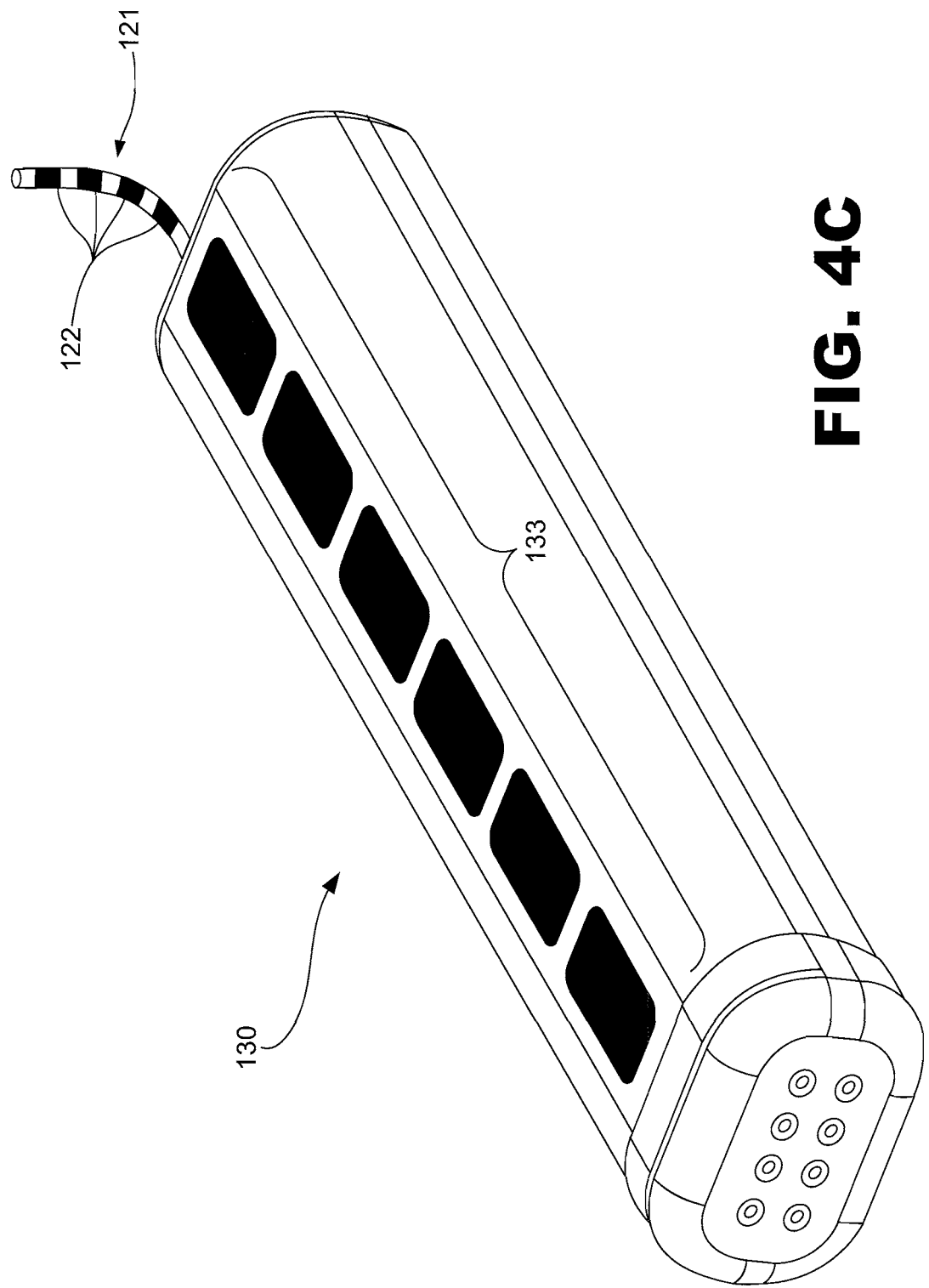
FIG. 4C shows the exemplary microstimulator of FIG. 4B coupled to a lead having a number of electrodes disposed thereon according to principles described herein.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 133 disposed on the outer surface thereof.

FIG. 4B illustrates an exemplary microstimulator 130 with a plurality of electrodes 133 disposed on an outer surface thereof. In some examples, any number of electrodes 133 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 133 and 122 may be selectively configured to serve as an anode or as a cathode.

In some examples, the stimulator 120 of FIG. 2 may be communicatively coupled to one or more wireless electrodes disposed at a stimulation site. For example, the stimulator 120 may be configured to wirelessly transmit signals representative of electrical stimulation to one or more stent electrodes or other types of electrodes. Exemplary stent electrodes that may be used in accordance with the systems and methods described herein are described in U.S. Patent Application Publication No. 20070150009, which application is incorporated herein by reference in its entirety.

Figure 5:
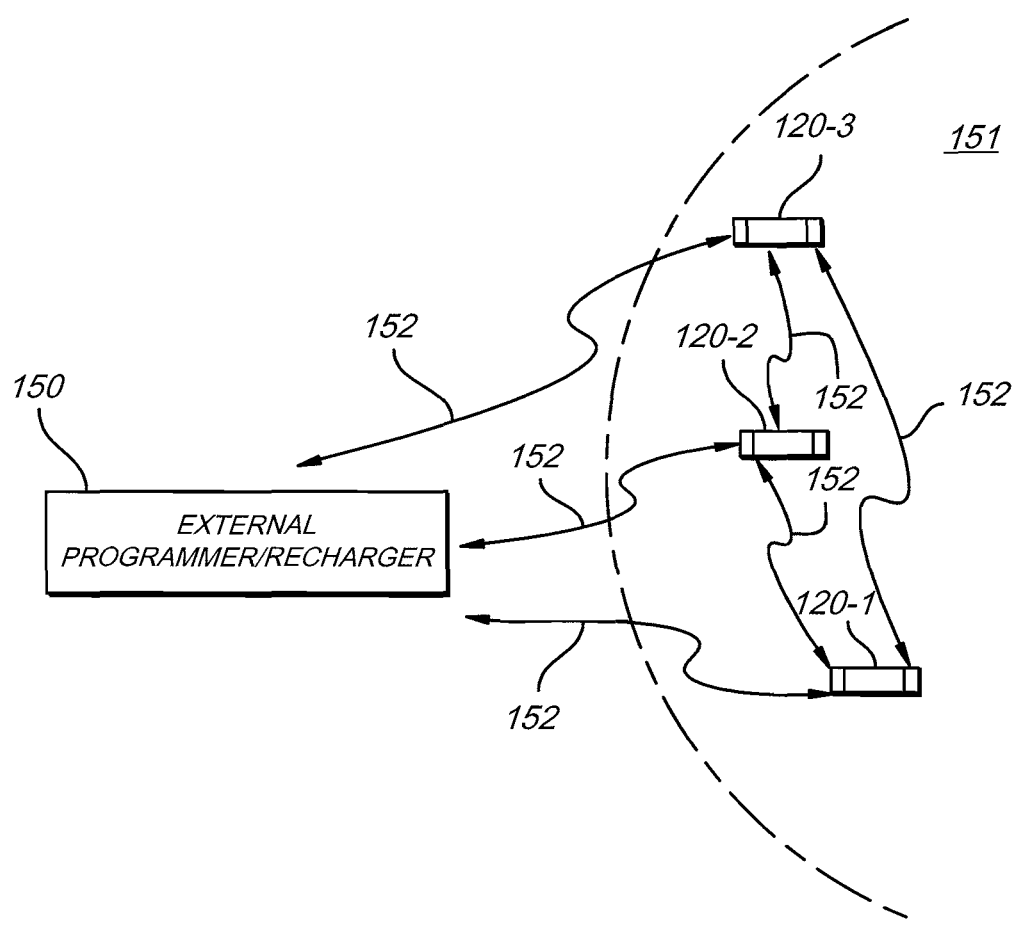
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the symptoms or causes of pancreatitis pain and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of pancreatitis pain, communicate or receive data regarding such indicators, and adjust stimulation parameters accordingly.

In order to determine the strength and/or duration of electrical stimulation and/or amount and/or type(s) of stimulating drug(s) required to most effectively treat pancreatitis pain, various indicators of pancreatitis pain and/or a patient's response to treatment may be sensed or measured. The stimulator 120 may then adjust the stimulation parameters (e.g., in a closed loop manner) in response to one or more of the sensed indicators. Exemplary indicators include, but are not limited to, neurotransmitter levels, patient input, changes in hormone concentration, detected stomach activity, circumference changes in the duodenum (e.g., as a result of peristalsis), pyloric sphincter contraction, detected food passing through the gastrointestinal tract, a change in one or more pH levels, audible sounds from the stomach (i.e., borborygmus), detected contraction of exocrine tissue around ductal occlusions, and pressure changes in the bile duct, pancreatic duct 101, ampulla, and/or duodenum 102. In some examples, the stimulator 120 may be configured to perform one or more of the measurements. Alternatively, other sensing devices may be configured to perform the measurements and transmit the measured values to the stimulator 120.

Examples of sensing devices that may be used as components of or in conjunction with the stimulator 120 include, but are not limited to, subcutaneous buttons (pressed by the user or a practitioner), hormonal or chemical sensors, piezoelectric sensors, strain gauges, optical sensors, pH detectors, auditory sensors, pressure sensors, and/or combinations thereof.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

By way of example, an exemplary method of treating pancreatitis pain may be carried out according to the following sequence of procedures. The steps listed below may be modified, reordered, and/or added to as best serves a particular application.

1. A stimulator 120 is implanted so that its electrodes 122 and/or infusion outlet 129 are in communication with a stimulation site within a patient. As used herein and in the appended claims, the term "in communication with" refers to the stimulator 120, stimulating electrodes 122, and/or infusion outlet 129 being adjacent to, in the general vicinity of, in close proximity to, directly next to, or directly on the stimulation site.

2. One or more stimulation parameters are configured to treat pancreatitis pain.

3. The stimulator 120 is programmed with the one or more stimulation parameters configured to treat pancreatitis pain.

The stimulator 120 may then generate and apply at least one stimulus to the stimulation site in accordance with the stimulation parameters. The stimulus may include electrical stimulation, drug stimulation, gene infusion, chemical stimulation, thermal stimulation, electromagnetic stimulation, mechanical stimulation, and/or any suitable stimulation.

3. When the patient desires to invoke stimulation, the patient sends a command to the stimulator 120 (e.g., via a remote control) such that the stimulator 120 delivers the prescribed stimulation to the stimulation site. For example, the stimulation may be activated by the patient when a particular incident of pancreatitis pain is detected. The stimulator 120 may alternatively or additionally be configured to apply the stimulation to the stimulation site in accordance with one or more pre-determined stimulation parameters and/or automatically apply the stimulation in response to sensed indicators of pancreatitis pain.

4. To cease or decrease stimulation, the patient may turn the stimulator 120 down or off (e.g., via a remote control).

5. Periodically, the power source 125 of the stimulator 120 is recharged, if necessary, in accordance with Function 1 described above.

In other examples, the treatment administered by the stimulator 120, i.e., drug therapy and/or electrical stimulation, may be automatic and not controlled or invoked by the patient. It will be recognized that the particular stimulation methods and parameters may vary as best serves a particular application.

Figure 6:
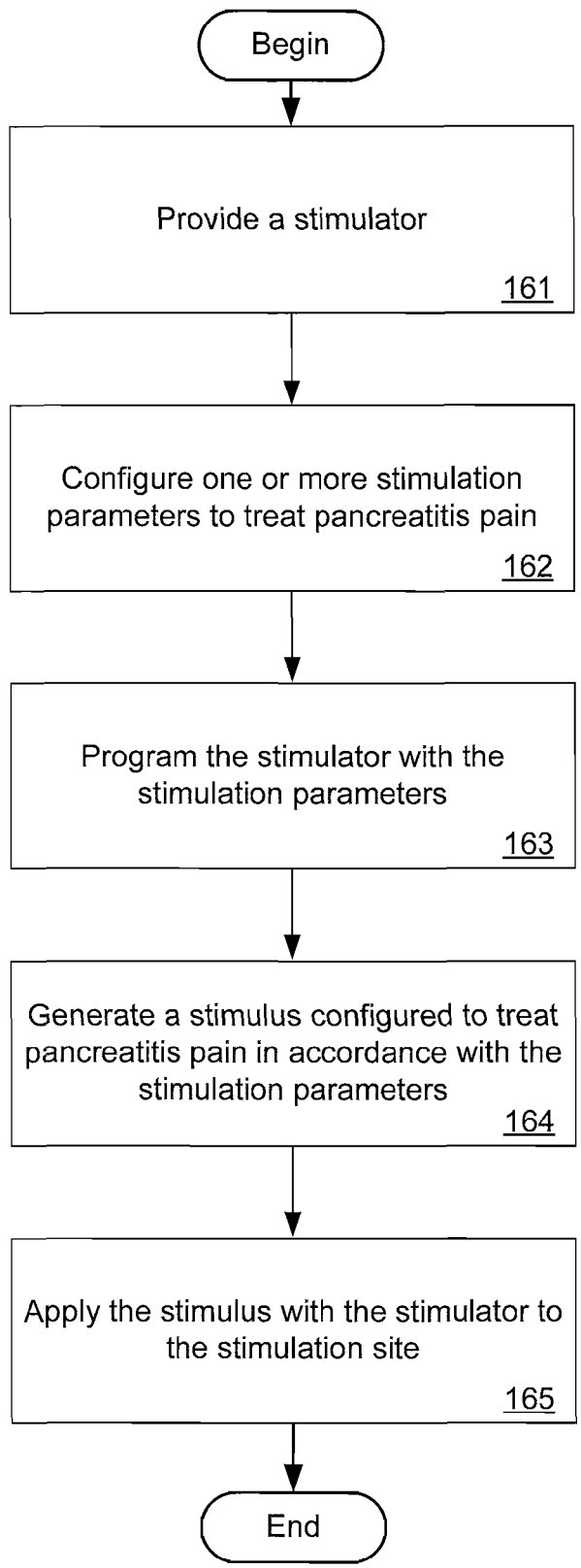
FIG. 6 is a flowchart of an exemplary method of treating pancreatitis pain according to principles described herein.

FIG. 6 shows a flowchart of an exemplary method of treating pancreatitis pain, according to the principles that have been described in more detail above. While FIG. 6 illustrates exemplary steps according to one embodiment, other embodiments may omit, add to, reorder, and/or modify any of the steps shown in FIG. 6.

In step 161, a stimulator is provided. In step 162, one or more stimulation parameters are configured to treat pancreatitis pain. In step 163, the stimulator is programmed with the stimulator parameters. In step 164, a stimulus configured to treat pancreatitis pain in accordance with the stimulation parameters is generated. In step 165, the stimulus is applied with the stimulator to the stimulation site.

The stimulator 120 may be implanted within a patient using any suitable surgical procedure such as, but not limited to, small incision, open placement, laparoscopy, or endoscopy. Exemplary methods of implanting a microstimulator, for example, are described in U.S. Pat. Nos. 7,193,539; 5,193,540; 5,312,439; 6,185,452; 6,164,284; 6,208,894; and 6,051,017. Exemplary methods of implanting an SCS, for example, are described in U.S. Pat. Nos. 7,501,703; 6,487,446; and 6,516,227. Exemplary methods of implanting a deep brain stimulator, for example, are described in U.S. Pat. Nos. 7,938,688; 6,016,449; and 6,539,263. All of these listed patents are incorporated herein by reference in their respective entireties.

To illustrate, FIGS. 7A-7D illustrate exemplary configurations wherein one or more electrodes 122 coupled to an implantable stimulator 120 have been implanted such that they are in communication with one or more stimulation sites within a patient. The configurations shown in FIGS. 7A-7D are merely illustrative of the many different implant configurations that may be used in accordance with the systems and methods described herein.

Figure 7A:
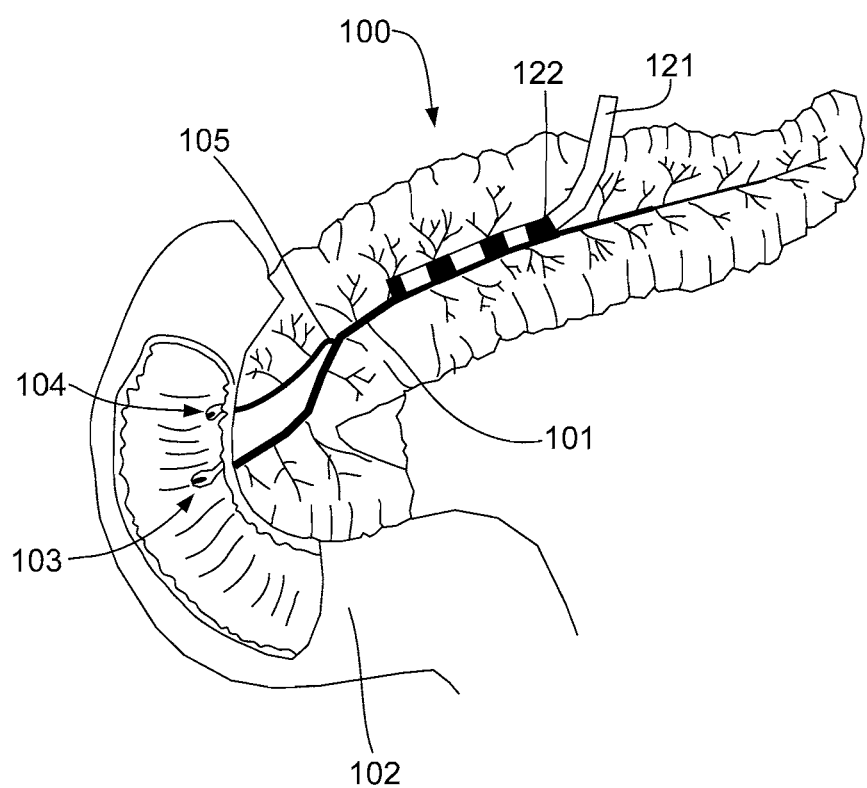
FIGS. 7A-7D illustrate exemplary configurations wherein one or more electrodes coupled to an implantable stimulator have been implanted such that they are in communication with one or more stimulation sites within a patient according to principles described herein.

In the example of FIG. 7A, the distal portion of a lead 121 having electrodes 122 disposed thereon may be placed along the pancreatic duct 101 such that the electrodes 122 are in communication with one or more of the regions or exocrine tissue in the general vicinity of the pancreatic duct 101 and/or one or more of the nerves that innervate the exocrine tissue. It will be recognized that although only an electrode lead 121 is shown in FIG. 7A, a catheter 123 may additionally or alternatively be implanted for drug stimulation in a similar manner.

The lead 121 shown in FIG. 7A may be coupled to a stimulator 120 that has been implanted in a more convenient location. For example, the stimulator 120 may be subcutaneously implanted within the abdomen. This may allow easy access to the stimulator 120 and maximize the efficiency of power recharging and/or data communication operations between the stimulator 120 and an external instrument.

In some alternative examples, an appropriately sized stimulator 120 with one or more electrodes 122 disposed thereon may be implanted at least partially within the pancreas 100.

In some examples, an expanded ply(tetrafluoroethylene) (PTFE) sheet containing one or more electrodes may be attached to the surface of the pancreas 100.

In this manner, a clot may be caused to form between the electrode array and the pancreas 100 so as to secure the electrodes at desired positions within the pancreatic tissue.

Figure 7B:
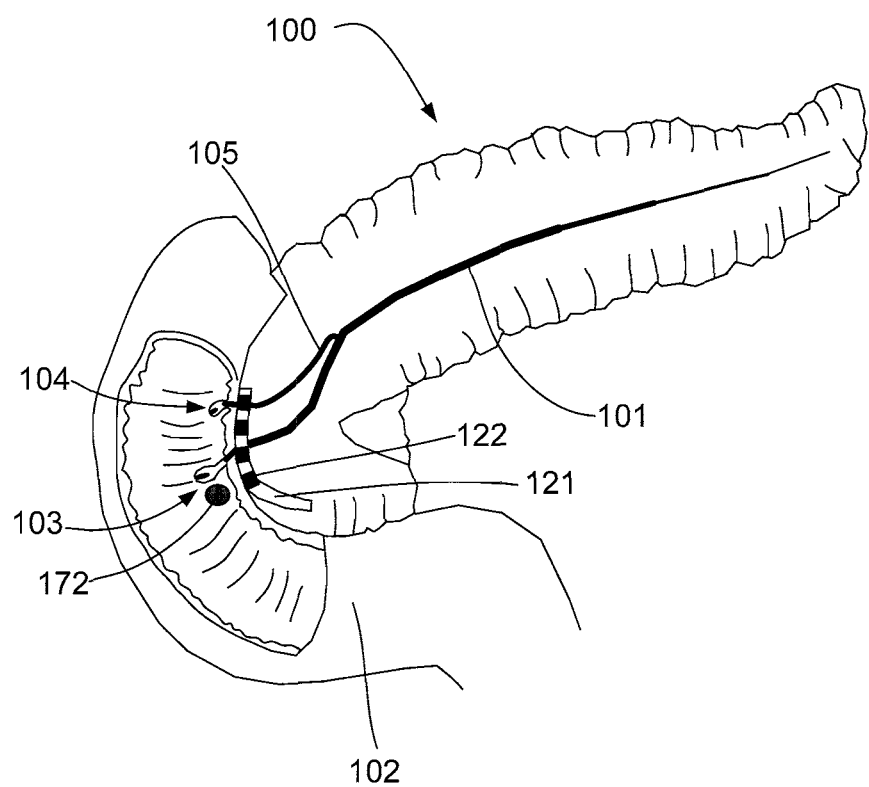

FIG. 7B shows a lead 121 having electrodes 122 disposed thereon placed at or near the tissue in the general vicinity of the major and minor duodenal papilla 103 and 104. A sensor 172 disposed within the duodenum may detect biological conditions, such as pH changes, enzyme concentrations, etc., that may provide feedback used to determine optimal stimulation parameters by the electrodes 122.

Figure 7C:
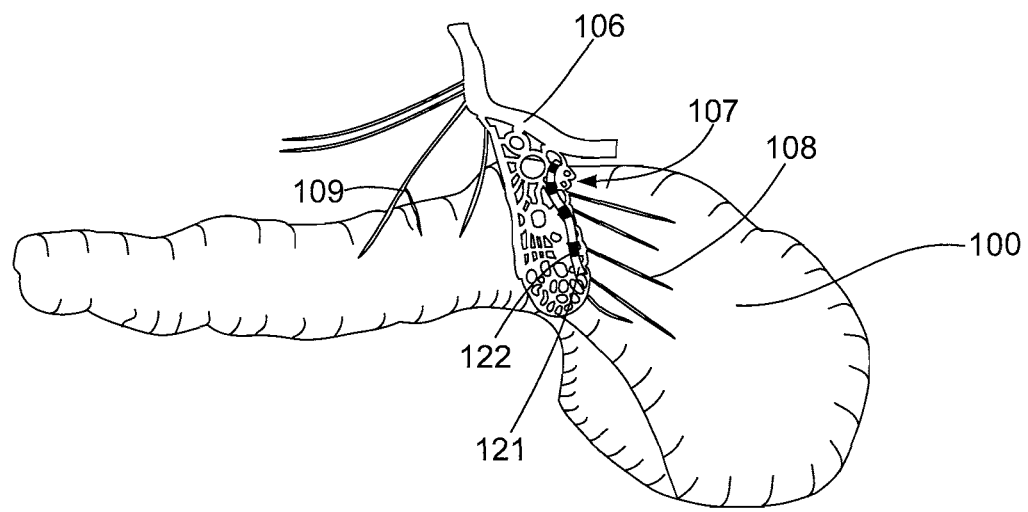
Figure 7D:
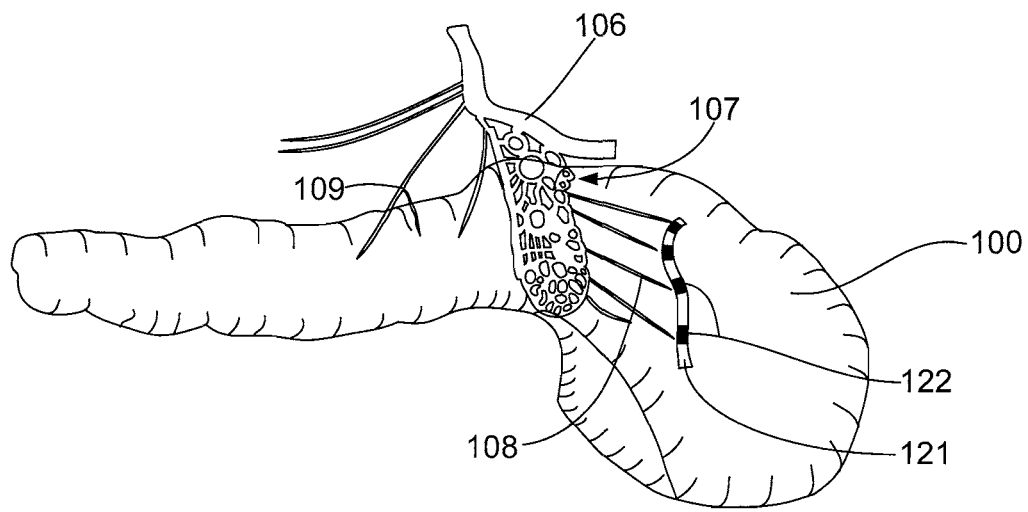

FIG. 7C shows an electrode lead 121 disposed at or near the nerve tissue of the celiac plexus 107, and FIG. 7D shows an electrode lead 121 placed at nerve branches of the celiac plexus 107 and/or celiac trunk 106 that innervate regions of the pancreas 100. It will be understood that the lead 121 and/or stimulator 120 may be implanted at any other suitable stimulation site as may serve a particular application.

Figure 8:
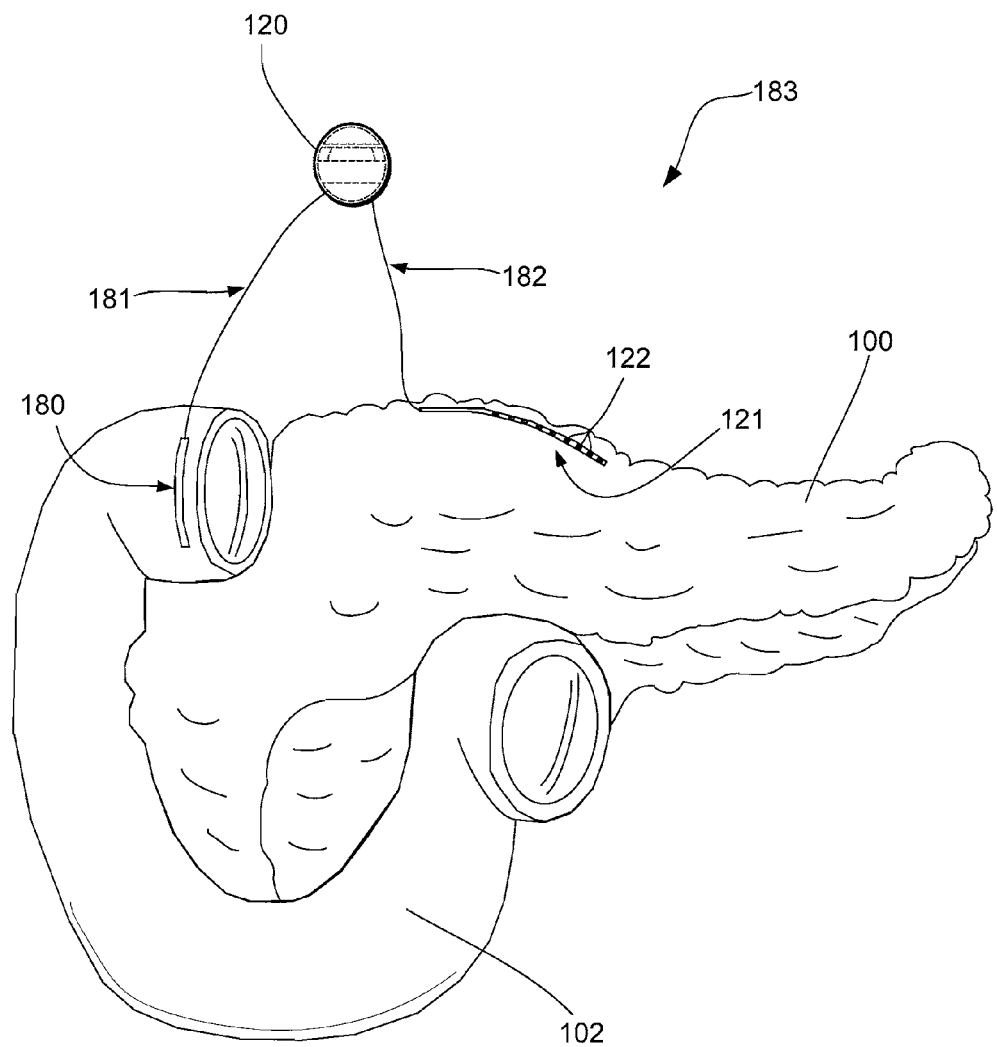
FIG. 8 illustrates an exemplary configuration wherein a sensing device is implanted within a patient and communicatively coupled to a stimulator according to principles described herein.

FIG. 8 illustrates an exemplary configuration wherein a sensing device 180 may be implanted within the patient and communicatively coupled to the stimulator 120. As shown in FIG. 8, a lead 121 having electrodes 122 may be disposed at a stimulation site within the patient (e.g., along a surface of the pancreas 100.) The sensing device 180 may be coupled to the duodenum 102, for example, or to any other tissue within the patient. The lead 121 and sensing element may be in electrical communication with the stimulator 120 through connections 181 and 182. The stimulator 120 may include electrical circuitry configured to interpret biological parameters detected by the sensing device 180 to determine optimal stimulation parameters.

The sensing device 180 shown in FIG. 8 may include any type of sensing device described herein. For example, the sensing device 180 may include a strain gauge or piezoelectric element configured to measure changes in the circumference of the duodenum 102.

Figure 9:
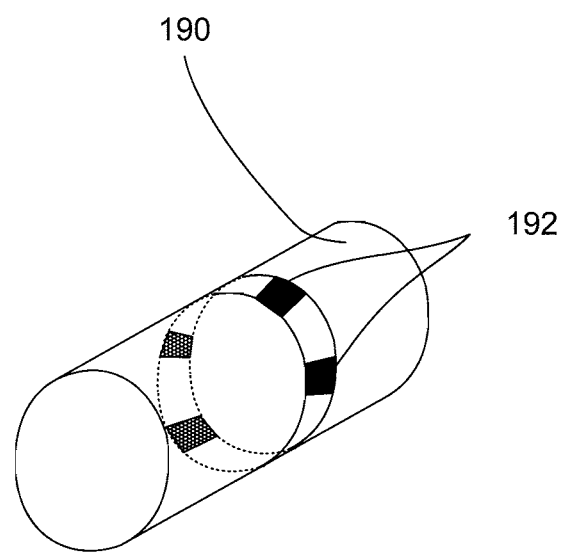
FIG. 9 illustrates an exemplary configuration wherein one or more electrodes are disposed on a stent according to principles described herein.

FIG. 9 shows an exemplary stent 190 that may be implanted within a patient in accordance with the systems and methods described herein. The stent may include one or more stent electrodes 192 disposed thereon through which electrical stimulation may be applied to one or more stimulation sites within the patient.

In some examples, the stent 190 may be implanted within pancreatic tissue, a pancreatic duct, a vein or artery associated with the pancreas, and/or any other location as may serve a particular application. The stent 190 may additionally or alternatively be implanted in any other suitable location within the patient. The body of stent 190 may be configured as an inductive loop antenna, for the purpose of receiving stimulation power and/or communication from an transmit antenna that is located external to the patient or is implanted within the patient.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with pancreatitis pain, comprising:
    generating a stimulus with a stimulator in accordance with one or more stimulation parameters; and
    applying the stimulus to a stimulation site comprising at least one or more of a pancreatic exocrine tissue, a pancreatic endocrine tissue, a nerve innervating the pancreatic exocrine tissue, a nerve innervating the pancreatic endocrine tissue, a pancreatic duct, a celiac trunk, a nerve surrounding or near the celiac trunk, a nerve surrounding or near a superior mesenteric vein or artery, a sympathetic trunk, and a somatic nerve, such that the pancreatitis pain is treated, wherein the application of the stimulus to the stimulation site suppresses production of one or more pancreatic enzymes.

2. The method of claim 1, wherein the application of the stimulus to the stimulation site reduces neural pain-inducing signals at the stimulation site.

3. The method of claim 1, wherein the stimulus comprises a stimulation current.

4. The method of claim 1, wherein the stimulus comprises an infusion of one or more drugs.

5. The method of claim 1, further comprising evaluating an effectiveness of the stimulus and adjusting the one or more stimulation parameters in accordance with the evaluation.

6. The method of claim 1, further comprising sensing at least one indicator related to the pancreatitis pain and using the at least one sensed indicator to adjust the one or more stimulation parameters.

7. The method of claim 6, wherein the indicator comprises at least one or more of a neurotransmitter level, a patient input, a change in hormone concentration, a detected stomach activity, a circumference change in a duodenum, a pyloric sphincter contraction, a detection of food passing through the gastrointestinal tract, a change in pH, an audible sound, a contraction of exocrine tissue, a pressure change in a bile duct, a pressure change in a pancreatic duct, a pressure change in an ampulla, and a pressure change in the duodenum.

8. The method of claim 1, further comprising implanting the stimulator within the patient.

9. The method of claim 1, wherein the stimulation site comprises pancreatic exocrine tissue.

10. The method of claim 1, wherein the stimulation site comprises pancreatic endocrine tissue.

11. The method of claim 1, wherein the stimulation site comprises a nerve innervating the pancreatic exocrine tissue.

12. The method of claim 1, wherein the stimulation site comprises a nerve innervating the pancreatic endocrine tissue.

13. The method of claim 1, wherein the stimulation site comprises a pancreatic duct.

14. The method of claim 1, wherein the stimulation site comprises a celiac trunk.

15. The method of claim 1, wherein the stimulation site comprises a nerve surrounding or near the celiac trunk.

16. The method of claim 1, wherein the stimulation site comprises a nerve surrounding or near a superior mesenteric vein or artery.

17. The method of claim 1, wherein the stimulation site comprises a sympathetic trunk.

18. The method of claim 1, wherein the stimulation site comprises a somatic nerve.

19. The method of claim 1, wherein the application of the stimulus to the stimulation site suppresses pancreatic digestive activity.

20. The method of claim 1, wherein the application of the stimulus to the stimulation site decreases pancreatic juice buildup.

21. The method of claim 1, wherein the stimulus comprises an infusion of at least one or more drugs, wherein the drug is at least one of a hormonal enzyme suppressant drug, a digestive enzyme suppressant drug, a drug that has an excitatory effect on the stimulation site and a drug that has an inhibitory effect on the stimulation site.

22. The method of claim 1, wherein the stimulation site is a nerve innervating pancreatic acinar cells.

23. The method of claim 1, wherein the application of the stimulus to the stimulation site blocks a vagal efferents that innervates acinar cells, thereby suppressing production of one or more pancreatic enzymes.

24. The method of claim 1, wherein the application of the stimulus to the stimulation site prevents contraction of exocrine tissue, thereby reducing obstructions at a pancreatic duct.

25. A method of treating a patient with pancreatitis pain, comprising:
generating a stimulus with a stimulator in accordance with one or more stimulation parameters; and
applying the stimulus to a stimulation site comprising at least one or more of a pancreatic exocrine tissue, a pancreatic endocrine tissue, a nerve innervating the pancreatic exocrine tissue, a nerve innervating the pancreatic endocrine tissue, a pancreatic duct, a celiac trunk, a nerve surrounding or near the celiac trunk, a nerve surrounding or near a superior mesenteric vein or artery, a dorsal root ganglion, a dorsal column, a dorsal root, a sympathetic trunk, a sympathetic ganglia, a spinal cord level, and a somatic nerve, such that the pancreatitis pain is treated, wherein the application of the stimulus to the stimulation site suppresses production of one or more pancreatic enzymes.

26. A method of treating a patient with pancreatitis pain, comprising:
generating a stimulus with a stimulator in accordance with one or more stimulation parameters; and
applying the stimulus to a stimulation site comprising at least one or more of a pancreatic exocrine tissue, a pancreatic endocrine tissue, a nerve innervating the pancreatic exocrine tissue, a nerve innervating the pancreatic endocrine tissue, a pancreatic duct, a celiac trunk, a nerve surrounding or near the celiac trunk, a nerve surrounding or near a superior mesenteric vein or artery, a dorsal root ganglion, a dorsal column, a dorsal root, a sympathetic trunk, a sympathetic ganglia, a spinal cord level, and a somatic nerve, such that the pancreatitis pain is treated, wherein the stimulus comprises an infusion of one or more drugs, wherein the drug is at least one of a hormonal enzyme suppressant drug, a digestive enzyme suppressant drug, a drug that has an excitatory effect on the stimulation site and a drug that has an inhibitory effect on the stimulation site.

* * * * *